(12) United States Patent
Heeney et al.

(10) Patent No.: US 6,943,275 B2
(45) Date of Patent: Sep. 13, 2005

(54) PROCESS OF PREPARING A DISUBSTITUTED 9-ALKYLIDENEFLUORENE OR A DERIVATIVE THEREOF

(75) Inventors: Martin Heeney, Southampton (GB); Steven Tierney, Southampton (GB); Mark Giles, Southampton (GB); Clare Bailey, Southampton (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/825,604

(22) Filed: Apr. 16, 2004

(65) Prior Publication Data

US 2004/0256616 A1 Dec. 23, 2004

Related U.S. Application Data

(60) Provisional application No. 60/469,392, filed on May 12, 2003.

(30) Foreign Application Priority Data

Apr. 16, 2003 (EP) ............................................. 03008726

(51) Int. Cl.$^7$ ........................... C07C 15/02; C07C 2/00; C07D 333/74
(52) U.S. Cl. .......................... 585/500; 585/400; 549/43
(58) Field of Search ................................ 585/500, 400; 549/43

(56) References Cited

U.S. PATENT DOCUMENTS

| | | | |
|---|---|---|---|
| 5,315,014 A | | 5/1994 | Ferraris et al. |
| 5,650,548 A | * | 7/1997 | Theriot et al. ............... 585/525 |
| 5,910,619 A | * | 6/1999 | Urata et al. .................. 585/513 |
| 5,962,631 A | * | 10/1999 | Woo et al. ................... 528/397 |
| 6,169,163 B1 | | 1/2001 | Woo et al. |
| 6,255,447 B1 | * | 7/2001 | Woo et al. ................... 528/397 |
| 6,329,492 B1 | * | 12/2001 | Sue et al. ...................... 528/97 |
| 6,344,585 B2 | * | 2/2002 | Mori ........................... 562/460 |
| 6,353,083 B1 | * | 3/2002 | Inbasekaran et al. ....... 528/295 |
| 6,363,310 B1 | * | 3/2002 | Schuplin et al. .............. 701/93 |
| 6,380,445 B1 | * | 4/2002 | Rietz et al. .................. 570/129 |
| 6,512,083 B1 | * | 1/2003 | Woo et al. ................... 528/397 |
| 6,593,450 B2 | * | 7/2003 | Woo et al. ................... 528/397 |
| 6,805,922 B2 | * | 10/2004 | Heeney et al. ............... 428/1.1 |
| 2003/0067267 A1 | | 4/2003 | Heeney et al. |

FOREIGN PATENT DOCUMENTS

| | | |
|---|---|---|
| EP | 1284258 | 2/2003 |
| WO | WO 00/46321 | 8/2000 |

OTHER PUBLICATIONS

P.D. Howes et al.: "Synthesis of 5,6–Dihydro–4H–1,3, 5–dithiazines, 2,3–dihydro–6–thioxo–6h–1,3–Thiazine, and 6–Amino–1,3–Dithins" Journal of the Chemical Society, Perkin Trans. I, vol. 1980, pp. 1038–1044.*

D. Villemin et al.: "A Convenient One–Pot Synthesis of Ketene Dithioacetals" Synthesis, vol. 4, 1991, pp. 301–303.*

J.F. Normant: "Stoichiometric Versus Catalytic Use of Copper (I) Salts in the Synthetic Use of Main Group Organometallics" Pure and Applied Chemistry, vol. 50, 1978, pp. 709–715.*

* cited by examiner

Primary Examiner—Deborah C. Lambkin
(74) Attorney, Agent, or Firm—Millen White Zelano & Branigan, P.C.

(57) ABSTRACT

The invention relates to a process of preparing disubstituted 9-alkylidenefluorenes and structure analogous compounds, to novel compounds and intermediates prepared by this process, their use for the preparation of conjugated polymers and copolymers thereof, and to novel polymers and copolymers thereby prepared.

14 Claims, No Drawings

PROCESS OF PREPARING A DISUBSTITUTED 9-ALKYLIDENEFLUORENE OR A DERIVATIVE THEREOF

This application claims the benefit of U.S. Provisional Patent Application No. 60/469,392, filed May 12, 2003.

The invention relates to a process of preparing disubstituted 9-alkylidenefluorenes and structure analogous compounds, and to novel compounds and intermediates prepared by this process. The invention further relates to the use of the compounds obtainable by the process for the preparation of conjugated polymers and copolymers thereof, and to novel polymers and copolymers thereby prepared. The invention further relates to use of the compounds and polymers as semiconductors or charge transport materials in optical, electrooptical or electronic devices including field effect transistors, electroluminescent, photovoltaic and sensor devices. The invention further relates to field effect transistors and semiconducting components comprising the novel compounds and polymers.

It is known in prior art that alkylidenefluorene (1) and poly(9-alkylidenefluorene) (2) are suitable for use as semiconductor and charge transport materials. These materials exhibit a high degree of planarity in the backbone due to the carbon $sp^2$ hybridization at the 9 position, in comparison with for example poly(9,9-dialkylfluorenes), and strong interchain pi-pi-stacking interactions, making them effective charge transport materials with high carrier mobilities. In addition, the high resonance stability of the fused phenylene structure leads to a high ionization potential and hence good stability. Also, the incorporation of alkyl substituents $R^1$ and $R^2$ into the alkylidenefluorene group leads to good solubility and thus good solution processibility of the materials according to the present invention. Solution processing during device manufacture has the advantage over vacuum deposition of being a potentially cheaper and faster technique.

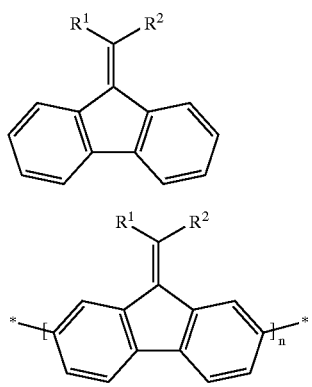

U.S. Pat. No. 6,169,163 discloses monosubstituted 9-alkylidenefluorenes (1) and poly(9-alkylidenefluorenes) (2) ($R^1$=alkyl, $R^2$=H). Copolymers of disubstituted 9-alkylidenefluorenes ($R^1$=$R^2$=alkyl optionally substituted) are disclosed in WO 00/46321, although no example or method for the preparation of monomer (1) is disclosed. The synthesis of specific monosubstituted 9-alkylidenefluorenes (1) ($R^1$=alkyl, $R^2$=H) is also described in K. Subba Reddy et al., *Synthesis*, 2000, 1, 165.

The synthesis of specific disubstituted 9-alkylidenefluorenes (1) ($R^1$=methyl, $R^2$=methyl or phenyl) is disclosed in K. C. Gupta et al., *Indian J. Chem., Sect. B*, 1986, 25B, 1067. This involves a Wittig type reaction between a 9-fluorenyl-phosphonium or phosphate salt and a ketone. The main drawback of this method, however, is the necessity to synthesize the starting Wittig reagent, and the expense and lack of availability of aliphatic ketones.

The synthesis of a specific copolymer of disubstituted 9-alkylidene-fluorene (1) ($R^1$=methyl, $R^2$=ethyl) is reported by M. Ranger and M. Leclerc, *Macromolecules* 1999, 32, 3306. According to this reference, the monomers (1) are prepared by the reaction of a secondary Grignard reagent with 2,7-dibromofluorenone, followed by dehydration of the resulting tertiary alcohol. However, this route is limited by the paucity of secondary Grignard reagents that are available.

Moreover, the methods of preparing disubstituted 9-alkylidene-fluorenes as disclosed in the above references of Gupta et al. and Ranger et al. are not readily amenable to the preparation of molecules with alkyl chains larger than propyl. Also, polymers of unsymmetrical 9-alkylidenefluorenes as disclosed in these references have the general problem of poor regioregularity and therefore poor ordering and packing in the solid state.

EP 1 284 258 A2 discloses novel mono-, oligo- and polymers of disubstituted 9-alkylidenefluorene. It also discloses a synthesis method that overcomes the problems outlined above by describing a new 3-step synthetic procedure for the preparation of monomers (1), as well as procedures for the preparation of polymers and co-polymers derived from (1). However, the reaction yields and reaction times of this method do still leave room for further improvement.

It was an aim of the present invention to provide an improved process for preparing disubstituted 9-alkylidenefluorene or structure analogous compounds, and oligo- or (co)polymers thereof.

Other aims of the present invention are immediately evident to the person skilled in the art from the following detailed description.

It was found that these aims can be achieved by a process of preparing disubstituted 9-alkylidenefluorenes according to the present invention as described below. In particular, this invention describes an improved process for the preparation of monomers (1) which has improved yields and reduced reactions times. It was also found that the process according to the present invention can be used to prepare aromatic compounds which are structure-analogous to 9-alkylidene-fluorene (1), like for example 4-alkylidenecyclopentadithiophenes (3).

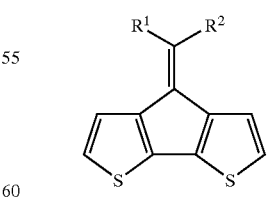

The compounds prepared by the process according to the present invention are especially useful for the preparation of oligo- and polymers or copolymers, like e.g. poly(9-alkylidenefluorenes), which are suitable as charge transport materials for semiconductor or light-emitting materials, components or devices.

SUMMARY OF THE INVENTION

The invention relates to a process of preparing a compound of formula I

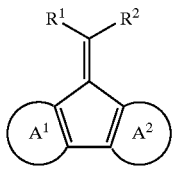

by
a) reacting a compound of formula Ia

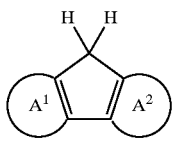

with a base in the presence of carbondisulfide or a dialkyl trithiocarbonate of the formula $[(R'S)_2CS]$ and an alkylating agent (R'X), and
b) reacting the resulting compound of formula Ib

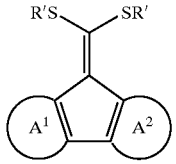

with a Grignard reagent $R^1MgX$ and/or $R^2MgX$ in the presence of a copper catalyst,
wherein
$A^1$ and $A^2$ are independently of each other an aromatic 5-, 6- or 7-membered ring which optionally contains one or more hetero atoms and is optionally substituted with one or more identical or different groups R,
R is halogen or has one of the meanings of $R^1$,
$R^1$ and $R^2$ are independently of each other straight chain, branched or cyclic alkyl with 1–20 C-atoms, which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —OCO—O—, —SO$_2$—, —S—CO—, —CO—S—, —CH=CH— or —C≡C— in such a manner that O and/or S atoms are not linked directly to one another, optionally substituted aryl or heteroaryl, or P-Sp,
$R^0$ and $R^{00}$ are independently of each other H or alkyl with 1 to 12 C-atoms,
P is a polymerizable or reactive group,
Sp is a spacer group or a single bond,
X is halogen, and
R' is straight, branched or cyclic alkyl with 1 to 20 C-atoms, which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —OCO—O—, —SO$_2$—, —S—CO—, —CO—S—, —CH=CH— or —C≡C— in such a manner that O and/or S atoms are not linked directly to one another, or alkyl aryl with up to 20 C-atoms.

More specifically, the invention relates to a process of preparing a compound of formula I1

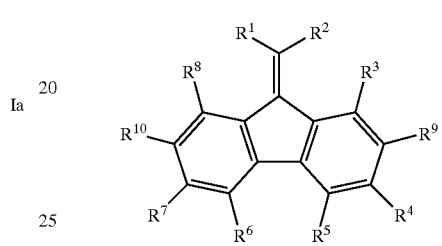

by
a) reacting a compound of formula I1a

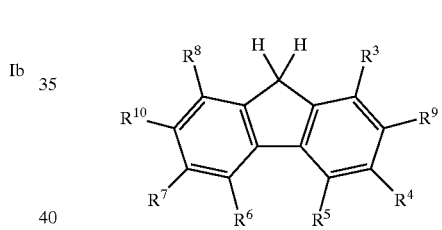

with a base in the presence of carbondisulfide or a dialkyl trithiocarbonate of the formula $[(R'S)_2CS]$ and an alkylating agent (R'X), and
b) reacting the resulting compound of formula I1b

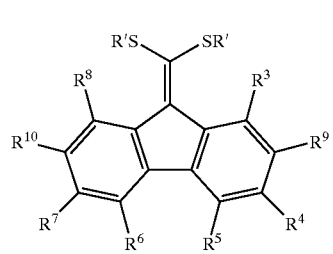

with a Grignard reagent $R^1MgX$ and/or $R^2MgX$ in the presence of a copper catalyst,
wherein $R^1$, $R^2$, R' and X have the meanings given above,
$R^3$ to $R^{10}$ are independently of each other H or have one of the meanings given for R, wherein at least one of $R^3$ to $R^8$, preferably $R^9$ and $R^{10}$, are independently of each other halogen.

Furthermore, the invention relates to a process of preparing a compound of formula I2

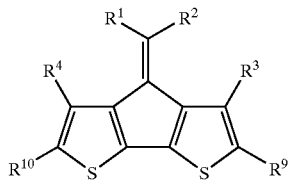

by
a) reacting a compound of formula I2a

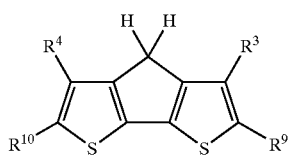

with a base in the presence of carbondisulfide or a dialkyl trithiocarbonate of the formula [(R'S)$_2$CS] and an alkylating agent (R'X), and
b) reacting the resulting compound of formula I2b

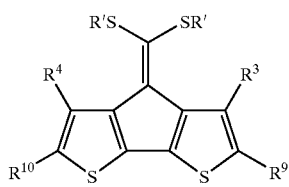

with a Grignard reagent R$^1$MgX and/or R$^2$MgX in the presence of a copper catalyst,
wherein R$^{1-4}$, R' and X have the meanings given above, and R$^9$ and R$^{10}$ are preferably independently of each other H or halogen.

The invention further relates to novel compounds and intermediates, in particular novel compounds of formula I, I1, I2, I1a, I1b, I2a and I2b, obtainable or obtained by the process or used in the process as described above and below.

The process according to the present invention offers significant advantages over the methods disclosed in prior art in terms of yield, number of reaction steps and synthetic flexibility. Thus for example various groups R$^1$ and R$^2$ can be readily incorporated. In particular, the process according to the present invention enables high yields and fast reaction times. In particular, the use of a copper catalyst has the advantage of lowering the reaction temperature, from reflux to temperatures down to 0° C., reducing the amount of alkyl grignard used, e.g. from 2.5 equivalents down to 2.2 equivalents, improving the yield and reducing the amount of byproducts, thereby aiding purification. In contrast, for example the use of Ni or Pd catalysts has the disadvantage that they can also catalyze the displacement of the bromine groups on the fluorene core.

The two-step process according to the present invention is exemplarily shown in Scheme 1 below. The first step involves the reaction of 2,7-dihalofluorene, preferably 2,7-dibromofluorene (4), which is a cheap and readily available starting material, with a base in the presence of carbon disulfide (CS$_2$) and an alkylating agent (R'X). This affords the dithioalkyl substituted fluorene (5) directly in one step. Alternatively to CS$_2$ a dialkyl trithiocarbonate of the formula [(R'S)$_2$CS] can be used, wherein R' is as defined above. In this case the alkylating agent (R'X) and the dialkyl trithiocarbonate [(R'S)$_2$CS] should comprised the same group R' (for example methyl). The alkylating agent R'X can be any primary alkyl or alkyl aryl halide. X is for example Cl, Br or I, preferably Br. R' is for example an alkyl or alkyl aryl group like methyl, hexyl or benzyl. (5) is then reacted with a Grignard reagent R$^1$MgX, wherein R$^1$ and X are as defined above, in the presence of a copper catalyst like for example Li$_2$CuCl$_4$, to form the disubstituted 9-alkylidenefluorene (6).

Scheme 1:

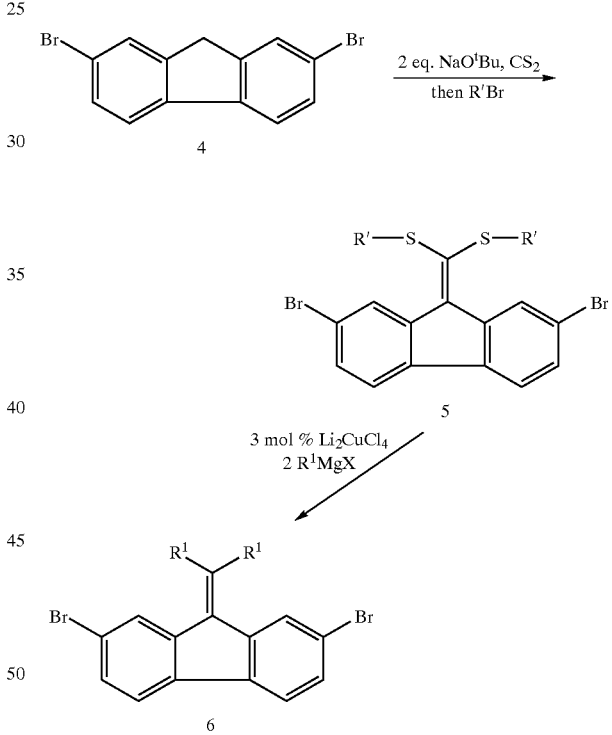

The preparation of structure analogous compounds, like for example 4-alkylidenecyclopentadithiophenes, is carried out in analogy to the above described process, and is exemplarily shown in Scheme 2 below. 2,6-Dibromocyclopentadienethiophene (7) is reacted with a base in the presence of carbon disulfide and an alkylating agent (R'X) to afford the dithioalkyl substituted compound (8), which is reacted with a Grignard reagent R$^1$MgX in the presence of a copper catalyst like for example Li$_2$CuCl$_4$ to form the disubstituted 4-alkylidenecyclopentadiene-thiophene (9).

Scheme 2:

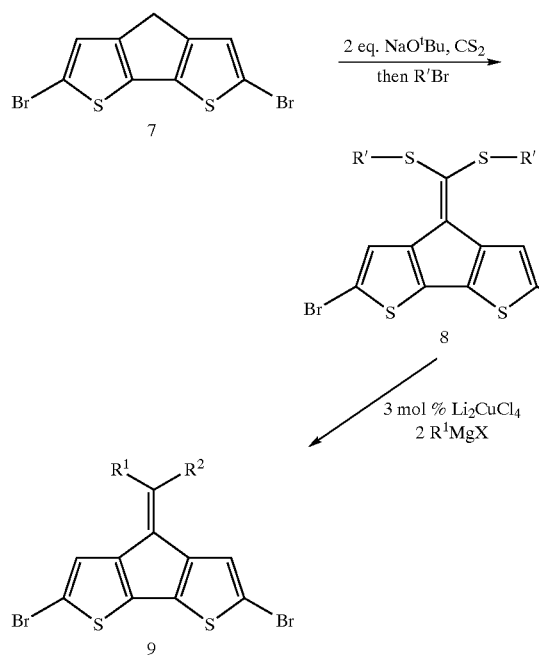

The starting materials and reagents used in the process according to the present invention are either commercially available (e.g. from Aldrich) or can be easily synthesized by methods well known to those skilled in the art.

Step a) of the inventive process is carried out in the presence of carbondisulfide ($CS_2$) or, more preferably, in the presence of a dialkyltrithiocarbonate of the formula [(R'S)$_2$ CS]. Therein, R' is preferably selected from methyl, ethyl or propyl, very preferably methyl.

The alkylating agent in step a) can be any alkylating agent, like for example an alkylhalogenide or alkyl aryl halogenide. Preferably it is selected of formula R'X, wherein X is halogen, preferably Cl, Br or I, very preferably Br or I, and R' is alkyl or alkyl aryl with 1 to 15 C-atoms. Very preferably it is selected from methyl iodide, ethyl bromide, propyl bromide, hexyl bromide or benzyl bromide, most preferably from methyl iodide, ethyl bromide or benzyl bromide. If a dialkyltrithiocarbonate of the formula [(R'S)$_2$ CS] is used in step a) then both groups R' should preferably be identical.

The base in step a) can principally any base of sufficient strength. Preferably it is selected from NaH, NaOtBut, KOtBut, KOH, NaOH, NaOMe, NaOEt, NaOtPent, KOtPent, very preferably from NaH, NaOtBut, KOtBut, or KOH.

Reaction step a) is preferably carried out in a dipolar aprotic solvent, which can be any solvent of this type, like for example DMSO, DMF, DMPU, DMAc or NMP.

The copper catalyst in step b) can be any catalyst that is suitable for a reaction involving organometallic reagents, and is preferably selected from CuI, CuBr or Li$_2$CuCl$_4$, most preferably Li$_2$CuCl$_4$.

The Grignard reagent in step b) can be any Grignard reagent, and is preferably of formula R$^1$MgX wherein X is Cl, Br or I, preferably Br or Cl. Preferably the Grignard reagent in step b) is added in an amount of from 2 to 3, very preferably 2 to 2.4, most preferably 2 to 2.2 equivalents of the thioalkyl substituted compound Ib, I1b or I2b, respectively.

Reaction step b) is preferably carried out in a polar aprotic solvent, which can be any solvent of this type, like for example THF, diethyl ether, dioxane, 1,2-dimethyoxyethane or tertbutylmethylether.

The process according to the present invention may be run at any temperature providing a sufficient conversion rate. It is preferred that the reaction is performed at a temperature between 0° C. and the solvent's reflux temperature, in particular at the temperatures as specified above and below. The reaction time depends on the actual rate of the individual reaction.

Preferably the reaction times are as given above and below.

For step a) the reaction temperature is preferably between 10° C. and 100° C., most preferably between 15° C. and 40° C. The reaction time is between 15 min and 24 h, most preferably between 30 min and 4 h. For step b) the reaction temperature is between −5° C. and reflux, most preferably between 0° C. and 30° C. The reaction times are between 3 h and 48 h, preferably between 3 h and 24 h.

The reaction products prepared by process according to the present invention may be isolated by usual work-up and purification with standard procedures well known to those skilled in the art. The crude product obtained in step a) can be directly used in step b) or can be purified before further reaction. The products obtained in step b) can be purified by known methods, or may also be used without further purification, for example for the preparation of polymers or copolymers.

Preferably, the process according to the present invention is carried out as follows:

Step a):

Dibromofluorene (3) or 2,6-dibromocyclopentadiene-thiophene (7) is dissolved in a dipolar aprotic solvent, like for example, DMSO, DMF or DMAc and stirred at room temperature (RT) or close to RT, for example 25° C., under an dry atmosphere, e.g. under nitrogen or dried air. More than 2 equivalents, preferably 2.1 equivalents, of base are added portionwise or as a solution in said solvent. Suitable and preferred bases include for example NaH, sodium tert-butoxide, finely ground KOH and potassium tert-butoxide. After stirring the reaction mixture for approximately 10 minutes, carbon disulfide or dimethyl trithiocarbonate (MeS)$_2$CS are added as neat liquids. Dimethyl trithiocarbonate is preferred over carbon disulfide because the latter has a flash point below 200° C., which can make larger scale processing problematic. The resulting solution is stirred for approximately 15 minutes, and then the alkylating agent, for example methyl iodide, ethyl bromide or benzyl bromide, is added neat. The reaction is stirred at RT for 1 h and then poured into water, and the resulting precipitate filtered to afford the crude product (>95%). The product can be recrystallized from THF for example or dried and used crude in the next step.

Step b):

Compound (5) or (7) is dissolved in THF, or an equivalent solvent like for example DME, diethyl ether etc., and cooled to 0° C. under an inert gas atmosphere of e.g. nitrogen. A solution of the copper catalyst, preferably Li$_2$CuCl$_4$, in a suitable solvent, like for example THF (preferably 3 mol % of a 0.1 M solution), is added, followed by more than 2, preferably 2.2 equivalents of a solution of alkyl or aryl Grignard reagent in THF or diethyl ether, in a concentration of typically 0.5 to 2M or more. The reaction is stirred for 4 h at 0° C. The reaction is quenched with dilute sodium hydroxide solution (preferably 5%), filtered, and extracted in THF or ethyl acetate. The solvent is removed under reduced pressure and the resulting solid recrystallized from a suitable solvent (for example petrol) to afford (6) or (9), respectively, with a yield of typically 60–80%.

Especially preferred are compounds of formula I, I1 and I2 wherein
- $A^1$ and $A^2$ are an aromatic 5-ring or 6-ring that optionally contains one or two hetero atoms selected from N, O and S,
- $A^1$ and $A^2$ are selected from benzene, thiophene or pyridine.
- $R^1$ and $R^2$ are identical (these can be obtained by using a single Grignard reagent $R^1MgX$ or $R^2MgX$ in step b),
- $R^1$ and $R^2$ are different (these can be obtained by using a mixture of two Grignard reagents $R^1MgX$ and $R^2MgX$ in step b),
- $R^1$ and $R^2$ are selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioalkyl, $C_1$–$C_{20}$-silyl, $C_1$–$C_{20}$-ester, $C_1$–$C_{20}$-amino, $C_1$–$C_{20}$-fluoroalkyl, or optionally substituted aryl or heteroaryl, in particular $C_1$–$C_{20}$-alkyl or $C_1$–$C_{20}$-fluoroalkyl,
- $R^3$ to $R^8$ are H,
- $R^1$ and $R^2$ are selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioalkyl, $C_1$–$C_{20}$-silyl, $C_1$–$C_{20}$-ester, $C_1$–$C_{20}$-amino, $C_1$–$C_{20}$-fluoroalkyl, or optionally substituted aryl or heteroaryl, in particular $C_1$–$C_{20}$-alkyl or $C_1$–$C_{20}$-fluoroalkyl, and $R^3$ to $R^8$ are H,
- $R^3$ to $R^8$ are selected from $C_1$–$C_{20}$-alkyl that is optionally substituted with one or more fluorine atoms, $C_1$–$C_{20}$-alkenyl, $C_1$–$C_{20}$-alkynyl, $C_1$–$C_{20}$-alkoxy, $C_1$–$C_{20}$-thioalkyl, $C_1$–$C_{20}$-silyl, $C_1$–$C_{20}$-ester, $C_1$–$C_{20}$-amino, $C_1$–$C_{20}$-fluoroalkyl, and optionally substituted aryl or heteroaryl,
- $R^9$ and $R^{10}$ are Cl, Br or I, very preferably Br.

Aryl and heteroaryl preferably denote a mono-, bi- or tricyclic aromatic or heteroaromatic group with up to 25 C atoms that may also comprise condensed rings and is optionally substituted with one or more groups $R^1$ as defined in formula I.

Especially preferred aryl and heteroaryl groups are phenyl in which, in addition, one or more CH groups may be replaced by N, naphthalene, thiophene, thienothiophene, dithienothiophene, alkyl fluorene and oxazole, all of which can be unsubstituted, mono- or polysubstituted with L, wherein L is halogen or an alkyl, alkoxy, alkylcarbonyl or alkoxycarbonyl group with 1 to 12 C atoms, wherein one or more H atoms may be replaced by F or Cl.

Arylene and heteroarylene preferably denote a bivalent mono-, bi- or tricyclic aromatic or heteroaromatic group with up to 25 C atoms that may also comprise condensed rings and is optionally substituted with one or more groups $R^1$.

Especially preferred arylene and heteroarylene groups are 1,4-phenylene in which, in addition, one or more CH groups may be replaced by N, naphthalene-2,6-diyl, thiophene-2,5-diyl, thienothiophene-2,5-diyl, dithienothiophene-2,6-diyl, alkyl fluorene and oxazole, all of which can be unsubstituted, mono- or polysubstituted with L as defined above.

$CX^1=CX^2$ is preferably —CH=CH—, —CH=CF—, —CF=CH—, —CF=CF—, —CH=C(CN)— or —C(CN)=CH—.

If in the formulae shown above and below one of $R^1$ to $R^8$ is an alkyl or alkoxy radical, i.e. where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Thioalkyl, i.e. where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridized vinyl carbon atom is replaced.

Fluoroalkyl is preferably $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

Halogen is preferably F, Br or Cl.

The polymerizable or reactive group P is preferably selected from $CH_2=CW^1$—COO—,

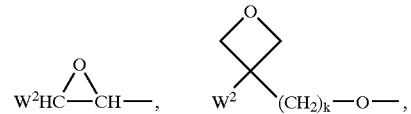

$CH_2=CW^2$—(O)$_{k1}$—, $CH_3$—CH=CH—O—, $(CH_2=CH)_2$CH—OCO—, $(CH_2=CH$—$CH_2)_2$CH—OCO—, $(CH_2=CH)_2$CH—O—, $(CH_2=CH$—$CH_2)_2$N—, $(CH_2=CH$—$CH_2)_2$N—CO—, HO—$CW^2W^3$—, HS—$CW^2W^3$—, $HW^2$ N—, HO—$CW^2W^3$—NH—, $CH_2=CW^1$—CO—NH—, $CH_2=CH$—(COO)$_{k1}$-Phe-(O)$_{k2}$—, Phe-CH=CH—, HOOC—, OCN—, and $W^4W^5W^6Si$ —, with $W^1$ being H, Cl, CN, phenyl or alkyl with 1 to 5 C-atoms, in particular H, $C_1$ or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene that is optionally substituted by one or more groups $R^1$ as defined above, and $k_1$ and $k_2$ being independently of each other 0 or 1.

Especially preferred groups P are $CH_2=CH$—COO—, $CH_2=C(CH_3)$—COO—, $CH_2=CH$—, $CH_2=CH$—O—, $(CH_2=CH)_2$CH—OCO—, $(CH_2=CH)_2$CH—O—, $(CH_2=CH$—$CH_2)_2$N—, $(CH_2=CH$—$CH_2)_2$N—CO— and

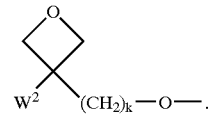

Very preferred are acrylate and oxetane groups. Oxetanes produce less shrinkage upon polymerization (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to the skilled in the art. The spacer group Sp is preferably of formula Sp'-X, such that P-Sp- is P-Sp'-X'-, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, X' is —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, and R$^0$ and R$^{00}$ have one of the meanings given above and Y$^1$ and Y$^2$ are, independently, H, F, Cl, or CN.

X' is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C— or a single bond, in particular —O—, —S—, —C≡C—, —CX$^1$=CX$^2$— or a single bond where X$^1$ and X$^2$ are, independently, H, F, Cl, or CN. In another preferred embodiment X' is a group that is able to form a conjugated system, such as —C≡C— or —CX$^1$=CX$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyl-iminoethylene, 1-methylalkylene, ethenylene, propenylene and butenylene for example.

Further preferred are compounds with one or two groups P-Sp- wherein Sp is a single bond.

In case of compounds with two groups P-Sp, each of the two polymerizable groups P and the two spacer groups Sp can be identical or different.

Another aspect of the invention is the use of compounds of formula I, I1 and I2 for the preparation of mono-, oligo- and polymers or copolymers thereof, in particular conjugated oligo- and (co)polymers.

Another aspect of the invention are mono-, oligo- and polymers or copolymers thereof, in particular conjugated oligo- and (co)polymers, obtainable from compounds of formula I, I1 and I2.

Oligo- and polymers can be prepared from the compounds of formula I, I1 and I2 by the methods as described in EP 1 284 258 A2 or the references cited therein.

Another aspect of the invention is a semiconductor or charge transport material, component or device comprising one or more compounds of formula I, I1 and I2 and mono-, oligo- and polymers or copolymers thereof, in particular conjugated oligo- and (co)polymers prepared thereof.

Another aspect of the invention is the use of compounds of formula I, I1 and I2 and mono-, oligo- and polymers or copolymers thereof, as semiconductors or charge transport materials, in particular in optical, electrooptical or electronic devices, like for example in field effect transistors (FET) as components of integrated circuitry, as thin film transistors in flat panel display applications or for Radio Frequency Identification (RFID) tags, or in semiconducting components for organic light emitting diode (OLED) applications such as electroluminescent displays or backlights of e.g. liquid crystal displays (LCD), for photovoltaic or sensor devices, as electrode materials in batteries, as photoconductors and for electrophotographic applications like electrophotographic recording.

Another aspect of the invention is the use of the compounds or mono-, oligo- or (co)polymers according to the invention as electroluminescent materials, in photovoltaic or sensor devices, as electrode materials in batteries, as photoconductors, for electrophotographic applications like electrophotographic recording and as alignment layer in LCD or OLED devices.

Another aspect of the invention is an optical, electrooptical or electronic device, FET, integrated circuit (IC), TFT, OLED or alignment layer comprising a semiconducting or charge transport material, component or device according to the invention.

Another aspect of the invention is a TFT or TFT array for flat panel displays, radio frequency identification (RFID) tag, electroluminescent display or backlight comprising a semiconducting or charge transport material, component or device or a FET, IC, TFT or OLED according to the invention.

Another aspect of the invention is a security marking or device comprising a FET or an RFID tag according to the invention.

The entire disclosures of all applications, patents and publications, cited herein and of corresponding European application No. 03008726.6, filed Apr. 16, 2003, and U.S. Provisional Application Ser. No. 60/469,392, filed May 12, 2003, are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

Preparation of 2,7-dibromo-9-(bis-methylsulfanyl-methylene)fluorene (by Reaction with carbon disulfide):

Sodium tert-butoxide (31.1 g, 0.32 mol) was added portionwise over 5 min to a solution of 2,7-dibromofluorene (50 g, 0.154 mol) in DMSO (1000 ml) at RT (22° C.) under nitrogen. To the resulting red solution was added carbon disulfide (13 g, 0.17 mol) via a syringe causing an exotherm to 35° C. The reaction was stirred for 10 min until the internal temperature was 30° C. Methyl iodide (46 g, 0.32 mol) was added over 2 min, causing an exotherm to 42° C. The reaction was stirred for 1 h and quenched by the addition of ice water (1000 ml) and conc. ammonia (20 ml). The reaction was stirred for 10 min and then filtered under reduced pressure and washed with further water (500 ml). After drying the crude yield was 64.8 g (98%, purity (HPLC) 97.8%). Recrystallization from ethyl acetate/THF (2:1)

afforded 55.2 g (purity (HPLC) 99.2%).): $^1$H and $^{13}$C NMR spectra as expected; M$^+$=428 (t). Anal. Calcd. For $C_{16}H_{12}Br_2S_2$: C, 44.9; H, 2.8, N, 0.0. Found C, 44.7; H, 3.1; N, <0.3.

EXAMPLE 2
Preparation of 2,7-dibromo-9-(bis-methylsulfanyl-methylene)fluorene (by Reaction with dimethyl trithiocarbonate):

Sodium tert-butoxide (1.24 g, 12.9 mmol) was added portionwise over 2 min to a solution of 2,7-dibromofluorene (2.0 g, 6.2 mmol) in DMSO (40 ml) at RT under nitrogen. To the resulting red solution was added dimethyl trithiocarbonate (0.94 g, 6.8 mmol) via a syringe. The reaction was stirred for 5 min and methyl iodide (1.8 g, 12.6 mmol) was added over 2 min. The reaction was stirred for 1 h worked up as above. Recrystallization from ethyl acetate/THF (2:1) afforded 2.4 g (91%). The sample was identical in all respects to that described above.

EXAMPLE 3
Preparation of 2,7-dibromo-9-(bis-hexylsulfanyl-methylene)fluorene:

A 60% dispersion of sodium hydride in mineral oil (0.26 g, 6.5 mmol) was added under nitrogen to 2,7-dibromofluorene (1.000 g, 3.09 mmol) in anhydrous dimethylsulfoxide (20 mL) at room temperature with stirring. The reaction mixture was stirred at room temperature for 10 minutes. Carbon disulfide (0.25 g, 0.2 mL, 3.3 mmol) was added via syringe and the reaction mixture was stirred at room temperature for 10 minutes. 1-Bromohexane (1.08 g, 6.5 mmol) was added and the reaction mixture was stirred at room temperature for 4 h. Ice-water (100 mL) was added and the resulting solid was filtered. The crude product was purified by recrystallization from iso-hexane to afford 1.225 g, (70%) as a bright yellow solid, purity 100% (GC): 1H and 13C NMR spectra as expected; M+=568 (t).

EXAMPLE 4
Preparation of 2,7-dibromo-9-(bisdecyl-methylene)fluorene:

To a solution of 2,7-dibromo-9-(bis-methylsulfanyl-methylene)fluorene (10.1 g, 23.5 mmol) in dry THF (150 ml) at 0° C. under nitrogen, was added a solution of lithium tetrachlorocuprate (5 ml of a 0.1M solution in THF, 2 mol %). A solution of decylmagnesium bromide (52 ml of a 1.0M solution in diethyl ether, 0.052 mol) was added dropwise over 30 min. The reaction was stirred for 2 h, during which time the internal temperature rose to 15° C. The reaction was cooled to 0° C. and further lithium tetrachlorocuprate (1 ml of a 0.1M solution in THF, 0.5 mol %) was added. The reaction was stirred a further 2 h, warming to 15° C., before quenching with 5% NaOH (100 ml). The reaction was stirred for 10 min and then filtered through celite. The organic layer was separated and the aqueous layer was further washed with ethyl acetate (100 ml). The combined organics were washed with brine (100 ml), dried (sodium sulfate), and concentrated under reduced pressure. The crude oil was further purified by filtration through a plug of silica (5 cm×5 cm) covered with a layer of basic alumina (1 cm×5 cm), eluting with petrol. After concentration, eicosane (formed from homocoupling of the Grignard reagent) was removed by distillation at reduced pressure and the residue was recrystallized from isohexane to afford 9.75 g of the product as white crystals (68%). Purity (HPLC>98%). $^1$H and $^{13}$C NMR spectra as expected; M$^+$=616 (t).

EXAMPLE 5
Preparation of 2,7-dibromo-9-(bishexyl-methylene) fluorene:

To a solution of 2,7-dibromo-9-(bis-methylsulfanyl-methylene)fluorene (5.1 g, 12 mmol) in dry THF (80 ml) at 0° C. under nitrogen, was added a solution of lithium tetrachlorocuprate (3 ml of a 0.1M solution in THF, 3 mol %). A solution of hexylmagnesium bromide (13 ml of a 2.0M solution in diethyl ether, 0.026 mol) was added dropwise over 30 min. The reaction was stirred for 2 h, during which time the internal temperature rose to 15° C. The reaction was cooled to 0° C. and further lithium tetrachlorocuprate (1 ml of a 0.1M solution in THF, 1 mol %) was added. The reaction was then stirred for 24 h at 25° C., before quenching and workup as above. Yield (61%). M.p 47–49° C. $^1$H and $^{13}$C NMR spectra as expected. M$^+$=504 (t). Anal. Calcd. For $C_{26}H_{32}Br_2$: C, 61.9; H, 6.4; N, 0.0. Found C, 61.8; H, 6.1; N, <0.3.

EXAMPLE 6
Preparation of 2,7-dibromo-9-(bisoctyl-methylene)fluorene:

To a solution of 2,7-dibromo-9-(bis-methylsulfanyl-methylene)fluorene (5.1 g, 12 mmol) in dry THF (100 ml) at 0° C. under nitrogen, was added a solution of lithium tetrachlorocuprate (5 ml of a 0.1 M solution in THF, 5 mol %). A solution of octylmagnesium bromide (13 ml of a 2.0M solution in diethyl ether, 0.026 mol) was added dropwise over 30 min. The reaction was stirred for 2 h at 5° C. The reaction was cooled to 0° C. and further lithium tetrachlorocuprate (1 ml of a 0.1M solution in THF, 1 mol %) was added. The reaction was then stirred for 24 h at 15° C., before quenching and workup as above. Yield (60%). Purity (HPLC>99%). $^1$H and $^{13}$C NMR spectra as expected. M$^+$=560 (t).

EXAMPLE 7
Preparation of 2,7-dibromo-9-(bisdodecyl-methylene) fluorene:

To a solution of 2,7-dibromo-9-(bis-methylsulfanyl-methylene)fluorene (4.28, 10 mmol) in dry THF (70 ml) at 0° C. under nitrogen, was added a solution of lithium tetrachlorocuprate (2 ml of a 0.1M solution in THF, 2 mol %). A solution of dodecylmagnesium bromide (22 ml of a 1.0M solution in diethyl ether, 0.022 mol) was added dropwise over 15 min. The reaction was stirred for 3 h at 0–5° C. before quenching with 5% NaOH (100 ml). The reaction was stirred for 10 min and then filtered through celite. The organic layer was separated and the aqueous layer further washed with ethyl acetate (100 ml). The combined organics were washed with brine (100 ml), dried (sodium sulfate), and concentrated under reduced pressure. The crude oil was further purified by filtration through a plug of silica (5 cm×5 cm) covered with a layer of basic alumina (1 cm×5 cm), eluting with petrol. After concentration the residue was recrystallized from isohexane to afford 4.2 of the product as white crystals (62%). Purity (HPLC>98%). $^1$H and $^{13}$C NMR spectra as expected.

EXAMPLE 8
Preparation of 2,7-dibromo-9-bis(6-methoxyhexyl-methylene)fluorene:

To a solution of 2,7-dibromo-9-(bis-methylsulfanyl-methylene)fluorene (8.60, 20.1 mmol) in dry THF (150 ml) at 0° C. under nitrogen, was added a solution of lithium tetrachlorocuprate (10 ml of a 0.1M solution in THF, 5 mol %). A solution of 6-methoxyhexylmagnesium bromide (50 ml of a 1.0M solution in THF, 0.05 mol) was added dropwise over 15 min. The reaction was stirred for 36 h at 20° C.

before quenching and workup as described above. Recrystallization from petrol afforded 8.5 g (75%) of the product. $^1$H and $^{13}$C NMR spectra as expected.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process of preparing a compound of formula I

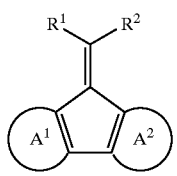

I comprising:

a) reacting a compound of formula Ia

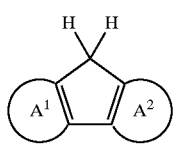

Ia with a base in the presence of carbondisulfide or a dialkyl trithiocarbonate of the formula [(R'S)$_2$CS] and an alkylating agent (R'X), and b) reacting the resulting compound of formula Ib

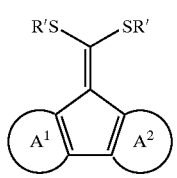

Ib with a Grignard reagent R$^1$MgX and/or R$^2$MgX in the presence of a copper catalyst, wherein A$^1$ and A$^2$ are, independently of each other, an aromatic 5-ring, 6-ring or 7-ring which optionally contains one or more hetero atoms and is optionally substituted with one or more identical or different groups R, R is halogen or has one of the meanings of R$^1$, R$^1$ and R$^2$ are, independently of each other, straight chain, branched or cyclic alkyl with 1–20 C-atoms, which may be unsubstituted, mono- or poly-substituted by F, Cl, Br, I or CN, optionally one or more non-adjacent CH$_2$ groups are replaced, independently from one another, by —O—, —S—, —NH—, —NR$^o$—, —SiR$^o$R$^{oo}$—, —CO—, —COO—, —OCO—, —OCO—O—, —SO$_2$—, —S—CO—, —CO—S—, —CH=CH— or —C≡C— in such a manner that O and/or S atoms are not linked directly to one another, optionally substituted aryl or heteroaryl, or P-Sp, R$^o$ and R$^{oo}$ are, independently of each other, H or alkyl with 1–12 C-atoms, P is a polymerizable or reactive group, Sp is a spacer group or a single bond, X is halogen, and R' is straight, branched or cyclic alkyl with 1–20 C-atoms, which may be unsubstituted, mono- or poly-substituted by F, Cl, Br, I or CN, optionally one or more non-adjacent CH$_2$ groups are replaced, independently from one another, by —O—, —S—, —NH—, —NR$^o$—, —SiR$^o$R$^{oo}$—, —CO—, —COO—, —OCO—, —OCO—O—, —SO$_2$—, —S—CO—, —CO—S—, —CH=CH— or —C≡C— in such a manner that O and/or S atoms are not linked directly to one another, or alkyl aryl with 1–20 C-atoms.

2. A process of preparing a compound according to claim 1, of formula I1

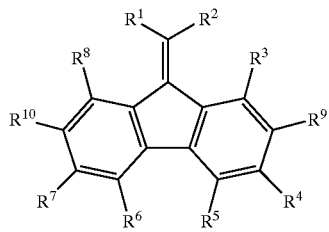

I1 comprising:

a) reacting a compound of formula I1a

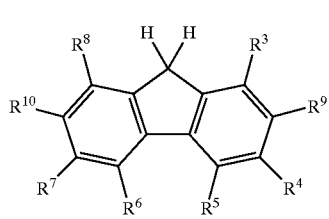

I1a with a base in the presence of carbondisulfide or a dialkyl trithiocarbonate of the formula [(R'S)$_2$CS] and an alkylating agent (R'X), and b) reacting the resulting compound of formula I1b

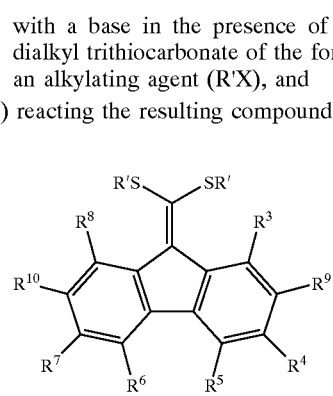

I1b with a Grignard reagent R$^1$MgX and/or R$^2$MgX in the presence of a copper catalyst, wherein R$^3$ to R$^8$ are, independently of each other, H, halogen, or have one of the meanings given for R$^1$, and R$^9$ and R$^{10}$ are, independently of each other, halogen.

3. A process of preparing a compound according to claim 1, of formula I2

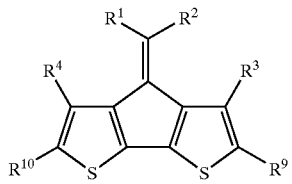

comprising:
a) reacting a compound of formula I2a

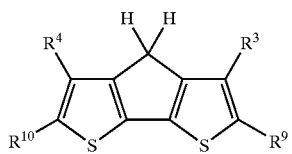

with a base in the presence of carbondisulfide or a dialkyl trithiocarbonate of the formula [(R'S)$_2$CS] and an alkylating agent (R'X), and b) reacting the resulting compound of formula I2b

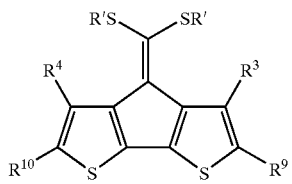

with a Grignard reagent R$^1$MgX and/or R$^2$MgX in the presence of a copper catalyst, wherein
R$^3$ to R$^4$ are, independently of each other, H, halogen, or have one of the meanings given for R$^1$, and
R$^9$ and R$^{10}$ are, independently of each other, H or halogen.

4. A process according to claim 1, wherein the alkylating agent in a) is an alkylhalogenide or alkyl aryl halogenide of formula R'X, wherein X is Cl, Br or I and R' is alkyl or alkyl aryl with 1–15 C-atoms.

5. A process according to claim 1, wherein the base in a) is NaH, KOH, NaOtbut, or KOtbut.

6. A process according to claim 1, wherein the copper catalyst in b) is Li$_2$CuCl$_4$.

7. A process according to claim 1, wherein the Grignard reagent in b) is R$^1$MgX wherein X is Cl, Br or I.

8. A process according to claim 1, wherein A$^1$ and A$^2$ are, independently, benzene, thiophene or pyridine.

9. A process according to claim 1, wherein R$^1$ and R$^2$ are, independently, C$_1$–C$_{20}$-alkyl, optionally substituted with one or more fluorine atoms, C$_1$–C$_{20}$-alkenyl, C$_1$–C$_{20}$-alkynyl, C$_1$–C$_{20}$-alkoxy, C$_1$–C$_{20}$-thioalkyl, C$_1$–C$_{20}$-silyl, C$_1$–C$_{20}$-ester, C$_1$–C$_{20}$-amino, or C$_1$–C$_{20}$-fluoroalkyl, or optionally substituted aryl or heteroaryl.

10. A process according to claim 1, wherein R$^9$ and R$^{10}$ are, independently, Cl, Br or I.

11. A process according to claim 1, wherein the reactive group P is CH$_2$=CW$^1$—COO—,

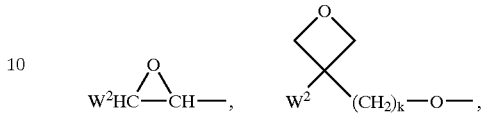

CH$_2$=CW$^2$—(O)$_{k1}$—, CH$_3$—CH=CH—O—, (CH$_2$=CH)$_2$ CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, Phe-CH=CH—, HOOC—, OCN—, or W$^4$W$^5$W$^6$Si—, wherein W$^1$ is H, Cl, CN, phenyl or alkyl with 1–5 C-atoms, W$^2$ and W$^3$ are, independently of each other, H or alkyl with 1–5 C-atoms, W$^4$, W$^5$ and W$^6$ are, independently of each other, Cl, oxaalkyl or oxacarbonylalkyl with 1–5 C-atoms, Phe is 1,4-phenylene that is optionally substituted by one or more groups R$^1$, and k$_1$ and k$_2$ are, independently of each other, 0 or 1.

12. A process according to claim 1, wherein the spacer group Sp is of the formula:

Sp'-X wherein:
Sp' is alkylene with up to 30 C atoms which is unsubstituted or mono- or polysubstituted by F, Cl, Br, I or CN, optionally one or more non-adjacent CH$_2$ groups are replaced, in each case, independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, X' is —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, and Y$^1$ and Y$^2$ have one of the meanings given above.

13. A process according to claim 1, wherein P is a polymerizable group.

14. A process according to claim 1, wherein P is a reactive group.

* * * * *